United States Patent
Zhang et al.

(10) Patent No.: US 10,023,882 B1
(45) Date of Patent: Jul. 17, 2018

(54) HETERO-OLIGOMERS OF (S)-CARBONYL REDUCTASES AND THEIR APPLICATIONS IN CATALYZING REDUCTION OF POLYPHENYL KETONES

(71) Applicants: Rongzhen Zhang, Wuxi (CN); Yan Xu, Wuxi (CN); Yaohui Li, Wuxi (CN)

(72) Inventors: Rongzhen Zhang, Wuxi (CN); Yan Xu, Wuxi (CN); Yaohui Li, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 15/641,268

(22) Filed: Jul. 4, 2017

(30) Foreign Application Priority Data

Mar. 13, 2017 (CN) .......................... 2017 1 0144938

(51) Int. Cl.
| | |
|---|---|
| *C12N 9/02* | (2006.01) |
| *C12P 7/02* | (2006.01) |
| *C12N 11/18* | (2006.01) |
| *C12P 7/22* | (2006.01) |
| *C12N 9/04* | (2006.01) |
| *C12P 17/12* | (2006.01) |

(52) U.S. Cl.
CPC .............. *C12P 7/22* (2013.01); *C12N 9/0006* (2013.01); *C12P 17/12* (2013.01); *C12Y 101/01184* (2013.01)

(58) Field of Classification Search
None
See application file for complete search history.

(56) References Cited

U.S. PATENT DOCUMENTS 9,422,583 B2 * 8/2016 Montelione .......... C12N 9/0006

OTHER PUBLICATIONS

Branden et al. (Introduction to Protein Structure, Garland Publishing Inc., New York, p. 247, 1991. (Year: 1991).*

* cited by examiner

*Primary Examiner* — Yong D Pak
(74) *Attorney, Agent, or Firm* — Lili Chen

(57) ABSTRACT

Provided are novel hetero-oligomers of (S)-carbonyl reductases and their application in catalyzing the reduction of polyphenyl ketones. Also provided are recombinant strains expressing hetero-oligomers of SCR/SCR2 or SCR2/SCR3, which can catalyze the reduction of polyphenyl ketones. The hetero-oligomer of SCR/SCR2 is capable of catalyzing 2,4-dichlorobenzophenone, 2-naphthalenone and [(E)-2-[3-[3-[2-(7-chloro-2-quinolinyl)ethenyl]phenyl]-3-oxopropyl] benzoic acid methyl ester (Keto Easter M) with a specific activity of 4.55 U/mg, 2.43 U/mg and 0.86 U/mg, respectively. The hetero-oligomer of SCR2/SCR3 is capable of catalyzing 2,4-dichlorobenzophenone and [(E)-2-[3-[3-[2-(7-chloro-2-quinolinyl)ethenyl]phenyl]-3-oxopropyl]benzoic acid methyl ester (Keto Easter M) with a specific activity of 4.42 U/mg and 1.21 U/mg, respectively. No catalyzing activities for reducing polyphenyl ketones were detected in the naturally existing homo-oligomers of SCR, SCR2 or SCR3, which can catalyze the reduction of monobenzoic cyclic compounds. The invention expands the substrate spectrum of natural (S)-carbonyl reductases (SCR, SCR2 and SCR3) and provides a novel type of oxidoreductases for catalyzing the reduction of polyphenyl ketones.

4 Claims, No Drawings

HETERO-OLIGOMERS OF (S)-CARBONYL REDUCTASES AND THEIR APPLICATIONS IN CATALYZING REDUCTION OF POLYPHENYL KETONES

CROSS-REFERENCES AND RELATED APPLICATIONS

This application claims priority of Chinese Application No. 201710144938.4, entitled "Novel hetero-oligomers of (S)-carbonyl reductases and their application in catalyzing the reduction of polyphenyl ketones", filed Mar. 13, 2017, which is herein incorporated by reference in its entirety.

BACKGROUND OF THE INVENTION

Field of the Invention

The present invention relates to the field of biocatalysis, and more particularly, relates to novel hetero-oligomers of (S)-carbonyl reductases and their application in catalyzing the reduction of polyphenyl ketones.

Description of the Related Art

Chiral compounds have been extensively used in the pharmaceutical, pesticides, hormones, food additives and other fine chemicals production. For example, 2-acetonaphthone is an important prochiral ketone which can be reduced to valuable drug precursors through biological methods, and [(E)-2-[3-[3-[2-(7-chloro-2-quinolinyl)ethenyl[phenyl]-3-oxopropyl]benzoic acid methyl ester (Keto Easter M) is a key intermediate for Montelukast Sodium.

Oxidoreductase-mediated asymmetric reductions are commonly used in the preparation of chiral compounds. Most of the commonly used oxidoreductases are produced from recombinant *Escherichia coli* (*E. coli*). The number and variety of stereoselective oxidoreductases used for industrial conversion of chiral alcohols are very limited, especially those in the production of (S)-chiral alcohols with anti-Prelog stereoselectivities. Therefore, there is a need to modify existing oxidoreductases to obtain novel functions to meet the requirement of industrial applications as well as to obtain more powerful biocatalysts for chiral synthesis.

Previously, we identified three (S)-carbonyl reductase genes, src, src2 and src3, in *Candida parapsilosis*. The (S)-carbonyl reductase members, naturally existed as homo-oligomers, can catalyze the linear aliphatic ketones and monobenzyclic ketones, but have no catalytic capacities towards biphenyl compounds and polyphenyl ketones. The recombinant *E. coli* containing one of the three (S)-carbonyl reductase genes could catalyze transformation of monobenzoic cyclic compounds such as 2-hydroxyacetphenone to (S)-1-phenyl-1,2-ethanediol, and, as expected, they cannot catalyze the reduction of polyphenyl ketones.

DETAILED DESCRIPTION

To solve the above problems, the present invention provides hetero-oligomers of different naturally existing carbonyl reductases that can expand the substrate spectrum of natural (S)-carbonyl reductases. Through the interactions between different members of (S)-carbonyl reductases (SCR, SCR2 and SCR3), the hetero-oligomers of carbonyl reductases can catalyze biphenyl compounds, such as 2,4-dichlorobenzophenone and 2-naphthoethanone, and polyphenyl ketones, such as [(E)-2-[3-[3-[2-(7-chloro-2-quinolinyl)ethenyl]phenyl]-3-oxopropyl]benzoic acid methyl ester (Keto Easter M).

The first goal of the present invention is to provide hetero-oligomers of carbonyl reductases capable of catalyzing polyphenyl ketones. The hetero-oligomer of (S)-carbonyl reductase herein refers to an oligomer of polypeptides from different (S)-carbonyl reductases that do not form an oligomer in their natural states, for example, an oligomer of polypeptides SCR/SCR2.

In one embodiment of the present invention, said hetero-oligomers of carbonyl reductases are formed by two or more (S)-carbonyl reductases with different amino acid sequences.

In one embodiment of the present invention, said (S)-carbonyl reductase is from *Candida parapsilosis* (*C. parapsilosis*).

In one embodiment of the present invention, said (S)-carbonyl reductase is SCR with an amino acid sequence shown in SEQ ID NO: 1, SCR2 with an amino acid sequence shown in SEQ ID NO: 2, or SCR3 with an amino acid sequence shown in SEQ ID NO: 3.

In one embodiment of the present invention, the genes encoding the (S)-carbonyl reductases are scr (GenBank ID: DQ675534), scr2 (GenBank ID: GQ411433) or scr3 (GenBank ID: FJ939564).

In one embodiment of the present invention, said hetero-oligomers of carbonyl reductases are either hetero-oligomer of SCR/SCR2 formed by SCR and SCR2, or hetero-oligomer of SCR2/SCR3 formed by SCR2 and SCR3.

In one embodiment of the present invention, said hetero-oligomer of carbonyl reductases is obtained by co-expressing two or more (S)-carbonyl reductases with different amino acid sequences in the same host.

The second goal of the invention is to provide a method of producing hetero-oligomers of (S)-carbonyl reductases. The method is to co-express two or more (S)-carbonyl reductases with different amino acid sequences in the same host.

In one embodiment of the present invention, two or more genes encoding (S)-carbonyl reductases with different amino acid sequences are ligated into an expression vector, and transformed into the same host to obtain a recombinant strain. The hetero-oligomers of (S)-carbonyl reductases are obtained through co-expression of two or more (S)-carbonyl reductases (SCR, SCR2 and SCR3).

In one embodiment of the present invention, the (S)-carbonyl reductase genes are ligated into the same expression vector or different vectors.

In one embodiment of the present invention, the expression vectors can be one or more of the following: pET21, pET28 and pETDuet.

In one embodiment of the present invention, the host is *E. coli, Saccharomyces cerevisiae, Pichia pastoris* or *Candida parapsilosis*.

In one embodiment of the present invention, the host is *E. coli* BL21 (DE3).

In one embodiment of the present invention, the genes are ligated onto an expression vector containing protein purification tags at the N-terminal of said (S)-carbonyl reductases.

In one embodiment of the present invention, said method comprises a protein purification procedure after co-expression of the hetero-oligomers of (S)-carbonyl reductases.

In one embodiment of the present invention, said method comprises the following steps: (1) obtaining two genes encoding different amino acid sequences of (S)-carbonyl reductases; (2) ligating the two (S)-carbonyl reductase genes onto different expression vectors, and constructing two recombinant plasmids containing two different (S)-carbonyl reductase genes with different N-terminal tags to facilitate protein purification; (3) transforming the two recombinant plasmids into the same host of E. coli BL21, resulting in two different amino acid sequences of (S)-carbonyl reductases co-expressed in the same host E. coli BL21 (DE3), and obtaining a recombinant E. coli; and (4) purifying the hetero-oligomers of (S)-carbonyl reductases in the recombinant E. coli.

In one embodiment of the present invention, said N-terminal tags of hetero-oligomers of (S)-carbonyl reductases are either His-tag, Strep-tag, GST-tag or MBP tag.

In one embodiment of the present invention, the protein purification of hetero-oligomers of (S)-carbonyl reductases with His-tag and Strep-tag is carried out as follows: disrupting the recombinant E. coli cells to obtain intracellular proteins, and centrifuging and collecting the supernatant; subjecting the supernatant to affinity chromatography on a Ni-NTA column; loading the eluate of 200 mM imidazole from the Ni-NTA column onto a Streptrap HP column; and collecting the purified hetero-oligomers of (S)-carbonyl reductases from the eluate of the Streptrap HP column.

In one embodiment of the present invention, the protein with a His-tag is purified by a Ni-NTA column. Since (S)-carbonyl reductases with different amino acid sequences can form as hetero-oligomers, (S)-carbonyl reductases with the Strep-tag would partially be bounded by the Ni-NTA column. Then the eluate from the Ni-NTA column was loaded onto a balanced Streptrap HP column, and finally the hetero-oligomers are eluted using a washing buffer containing 40 mM Tris-HCl with 2.5 mM desthiobiotin from the Streptrap HP column.

In one embodiment of the present invention, said method is as follows: each (S)-carbonyl reductase gene (scr, scr2 and scr3) derived from C. parapsilosis are ligated into an expression vector to obtain recombinant plasmids, pET21-Strep-SCR, pET28-His-SCR2, pET21-Strep-SCR2 and pET28-His-SCR3. The plasmids pET21-Strep-SCR and pET28-His-SCR2 are co-transformed into the same host E. coli BL21. The plasmids pET21-Strep-SCR2 and pET28-His-SCR3 are co-transformed into the same host E. coli. Then recombinant E. coli containing the two different plasmids are screened using both Ampicillin and kanamycin resistance. The recombinant E. coli strains containing pET21-Strep-SCR and pET28-His-SCR2 or pET21-Strep-SCR2 and pET28-His-SCR3 are thus obtained. Hetero-oligomers of (S)-carbonyl reductases are obtained from the fermentation of the above recombinant E. coli.

In one embodiment of the present invention, said fermentation is carried out as follows: the recombinant E. coli containing pET21-Strep-SCR and pET28-His-SCR2 or pET21-Strep-SCR2 and pET28-His-SCR3 are cultivated in a LB medium with 100 µg/ml Ampicillin and 50 µg/ml kanamycin at 37° C. and 200 rpm. When $OD_{600}$ of the culture is 0.6-0.8, 0.5 mM IPTG is added to induce the protein expression, the culture is continued for 12 hr.

The third goal of the present invention is to provide a recombinant strain expressing said hetero-oligomers.

In one embodiment of the present invention, said recombinant strain is constructed by the ligation of the (S)-carbonyl reductases with different amino acid sequences into different expression vectors, and the obtained recombinant expression vectors are co-transformed into the same host.

In one embodiment of the present invention, the host is E. coli, Saccharomyces cerevisiae, Pichia pastoris or Candida parapsilosis.

In one embodiment of the present invention, the host is E. coli BL21 (DE3).

In one embodiment of the present invention, the expression vector is one of the following: pET21, pET28 and pETDuet.

In one embodiment of the present invention, the genes ligated to the expression vectors contain the N-terminal tags for purification of (S)-carbonyl reductases.

The fourth goal of the present invention is to provide an application method of the hetero-oligomers of (S)-carbonyl reductases.

In one embodiment of the present invention, the application method is carried out by using the hetero-oligomers of (S)-carbonyl reductases in biocatalysis.

In one embodiment of the present invention, the application method is to apply the hetero-oligomers of (S)-carbonyl reductases to the production of fine chemistry.

In one embodiment of the present invention, the application method is to apply the hetero-oligomers of (S)-carbonyl reductases to catalyze the reduction of polyphenyl ketones.

In one embodiment of the present invention, said polyphenyl ketones include biphenyl compound and polyphenyl ketones.

In one embodiment of the present invention, said biphenyl compound is 2,4-dichlorobenzophenone or 2-acetonaphthone.

In the present invention, hetero-oligomers are obtained by co-expressing two or more different (S)-carbonyl reductase genes (scr, scr2 and scr3). Said hetero-oligomers have new properties, that is, catalysis of the polyphenyl ketones with good catalytic activities. The hetero-oligomers of this invention can be used in the field of fine chemical production.

According to the gene sequences of scr (GenBank ID: DQ675534), scr2 (GenBank ID: GQ411433) and scr3 (GenBank ID: FJ939564) from C. parapsilosis, recombinant E. coli strains are constructed harboring recombinant plasmids containing different (S)-carbonyl reductase genes. The hetero-oligomers are purified via different affinity tags on the polypeptides using pull-down experiments. The activities of hetero-oligomers towards the polyphenyl ketones, 2,4-dichlorobenzophenone, 2-naphthyl ketone and [(E)-2-[3-[3-[2-(7-chloro-2-quinolinyl)ethenyl[phenyl]-3-oxopropyl] benzoic acid methyl ester are determined, while no specific activity is observed in the homo-oligomers, such as SCR, SCR2 and SCR3. The hetero-oligomer of SCR/SCR2 is capable of catalyzing the reduction of 2,4-dichlorobenzophenone with a specific activity of 4.55 U/mg, 2-naphthalenone with a specific activity of 2.43 U/mg, and [(E)-2-[3-[3-[2-(7-chloro-2-quinolinyl)ethenyl[phenyl]-3-oxopropyl] benzoic acid methyl ester (Keto Easter M) with a specific activity of 0.86 U/mg; the hetero-oligomer of SCR2/SCR3 is capable of catalyzing the reduction of 2,4-dichlorobenzophenone with a specific activity of 4.42 U/mg, and [(E)-2-[3-[3-[2-(7-chloro-2-quinolinyl)ethenyl[phenyl]-3-oxopropyl]benzoic acid methyl ester (Keto Easter M) with a specific activity of 1.21 U/mg.

EXAMPLES

Determination of enzyme activity of homo-oligomer carbonyl reductases of different substrates:

(1) Principle and definition: The enzyme activity for the reduction of prochiral ketones to chiral alcohols by homo-oligomers was determined with purified enzymes by measuring the decrease in absorbance at 340 nm resulting from the oxidation of NADPH. Protein concentration was determined by Beyotime (Shanghai, China) using bovine serum albumin as a standard.

(2) Enzyme activity assay conditions (250 ul): 0.5 mmol·L$^{-1}$ NADPH, 1 mmol·L$^{-1}$ substrate (2,4-dichlorobenzophenone, 2-naphthyl ketone, or [(E)-2-[3-[3-[2-(7-chloro-2-quinolinyl)ethenyl]phenyl]-3-oxopropyl]benzoic acid methyl ester (Keto Easter M.).). Incubate the mixture at 30° C. for 2 min, then add appropriate amount of enzyme, and finally measure the absorbance at 340 nm wavelength.

(3) Calculation method and definition of enzyme activity

Formula for calculating enzyme activity is: Enzyme activity (U)=EW×V×10$^3$/(6220×0.15), and formula for calculating relative enzyme activity is: relative enzyme activity (U/mg)=enzyme activity (U)/protein content (mg), wherein EW is the measured change of absorbance at 340 nm in 1 min; V is the reaction volume (mL); the molar absorption coefficient (L mol$^{-1}$ cm$^{-1}$) is 6220; and the optical length is 0.15 cm.

One unit of the enzyme activity is defined as the amount of enzyme catalyzing the formation and oxidation of 1 μmol of NAD(P)H per minute under measurement conditions.

Example 1: Culture of C. Parapsilosis CCTCC M203011

The growth media of C. parapsilosis CCTCC M203011 contained 2% glucose, 1% yeast extract and 2% peptone. C. parapsilosis was inoculated to 5 mL liquid growth media and cultivated at 28° C. with 200 rpm shaking for 16-18 hr.

Example 2: Extraction of C. parapsilosis Genome

The C. parapsilosis cells obtained from Example 1 were centrifuged at 6,000 rpm for 5 min, washed twice, and then the cells were harvested for the extraction of genomic DNA using the Genomic DNA Mini Preparation Kit (Takara Co., Tokyo, Japan).

Example 3: Primers of Cloning of Scr, Scr2 and Scr3 Genes

The target gene sequences, including scr (the encoded amino acid sequence is shown in SEQ ID NO: 1), scr2 (the encoded amino acid sequence is shown in SEQ ID NO: 2) and scr3 (the encoded amino acid sequence is shown in SEQ ID NO: 3), were cloned from C. parapsilosis genome.

Primers synthesis (sequence as sequentially shown in SEQ ID NO:4 to SEQ ID NO: 11):

B-S-SCR-F1: atcggatccgtggtctcatcctcaatttgaaaagggttctatgggcgaaa tcgaatctta

X-S-SCR-R1: tgactctcgagctatggacacgtgtatccacc

B-S-SCR2-F1: atcggatccgtggtctcatcctcaatttgaaaagggttctatgggcgaaatcgaatctta

X-S-SCR2-R1: tgactctcgagctatggacaagtgtaaccaccat

B-His-SCR2-F1: cgcggatccgaaaatttatatttccagagtatgggcgaaatcgaatctta

X-His-SCR2-R1: tgactctcgagctatggacacgtgtatccacc

E-His-SCR3-F1: ccggaattcgaaaatttatatttccagagtatgggcgaaatcgaatctta

X-His-SCR3-R1: gcccgctcgagctatggacaggtgaatccaccatc

Example 4: Cloning of Scr, Scr2 and Scr3 Genes 50 uL PCR reaction system for cloning scr, src2 or scr3 genes contained 1 uL genomic DNA (20 ng), 2 uL primers (0.5 μM), 25 uL PrimeSTAR HS premix and 22 uL sterile ultra-pure water. PCR conditions were: 98° C. 10 s; (98° C. 10 s, 52° C. 15 s, 72° C. 1 min)×30 cycles, and 72° C. for 10 min. DNA fragments were purified using the 3S Spin Agarose Gel DNA Purification Kit (Shanghai Shenergy Gobi Biotechnology Co., Ltd.).

Primers of B-S-SCR-F1 and X-S-SCR-R1 were used for the amplification of scr gene with a Strep-tag at 5'-terminal to obtain a strep-scr gene. Primers of B-S-SCR2-F1 and X-S-SCR2-R1 were used for the amplification of scr2 gene with a Strep-tag at 5'-terminal to obtain a strep-scr2 gene. Primers of B-His-SCR2-F1 and X-His-SCR2-R1 were used for the amplification of scr2 gene with a His-tag at 5'-terminal to obtain a his-scr2 gene. Primers of E-His-SCR3-F1 and X-His-SCR3-R1 were used for the amplification of scr2 gene with His-tag at 5'-terminal to obtain a his-scr3 gene.

Example 5: Construction of Recombinant Plasmids Containing (S)-Carbonyl Reductase Genes The pET21 plasmid and the strep-scr gene were digested with BamH I and Xho I, respectively. The digested pET21 and strep-scr were ligated, transformed and verified, and finally the positive plasmid pET21-Strep-SCR was obtained. The pET21 plasmid and strep-scr2 genes were digested with BamH I and Xho I, respectively. The digested pET21 and strep-scr2 were ligated, transformed and verified, and finally the positive plasmid pET21-Strep-SCR2 was obtained. The plasmid pET28 and his-scr2 genes were digested with BamH I and Xho I, respectively. The digested pET28 and his-scr2 were ligated, transformed and verified, and finally the positive plasmid pET28-His-SCR2 was obtained. The pET28 and his-scr3 genes were digested with EcoR I and Xho I, respectively. The digested pET28 and his-scr3 were ligated, transformed and verified, and finally the positive plasmid pET28-His-SCR3 was obtained.

Example 6: Construction of Recombinant E. coli Expressing the Hetero-Oligomers Plasmid mini Kit I (200) (OMEGA, Norwalk, USA) was used to extract plasmids pET21-Strep-SCR, pET21-Strep-SCR2, pET28-His-SCR2 and pET28-His-SCR3 from recombinant E. coli JM109.

0.5 μL pET21-Strep-SCR and 0.5 μL pET28-His-SCR2 were added to 100 μL E. coli BL21 (DE3) competent cells, or 0.5 μL pET21-Strep-SCR2 and pET28-His-SCR3 were added to 100 μL E. coli BL21 (DE3) competent cells. The plasmids and E. coli competent cells were mixed gently and incubated on ice for 30 min. The heat shock was carried out at 42° C. for 90 sec. They were quickly put on ice for 2 min, and were incubated at 37° C. with 100 rpm for 1 hour after the addition of 700 μL LB liquid medium. The culture was centrifuged at 5,000 rpm for 1 min, and about 600 μL supernatant was removed. The remained bacteria and medium was mixed and applied to a LB medium plate containing 100 μg/mL Ampicillin and 50 μg/mL kanamycin, and incubated overnight. The recombinant E. coli harboring the plasmids pET21-Strep-SCR and pET28-His-SCR2 (named E. coli/pET21-Strep-SCR/pET28-His-SCR2) or recombinant E. coli harboring the plasmids pET21-Strep-SCR2 and pET28-His-SCR3 (named E. coli/pET21-Strep-SCR2/pET28-His-SCR3) were screened after 12 hr cultivation with both ampicillin and kanamycin resistance.

Example 7: Cultivation and Cell Collection of Recombinant E. Coli

The medium (LB medium) for the cultivation of recombinant E. coli contained 1% sodium chloride, 1% peptone and 0.5% yeast extract supplemented with 100 μg/mL ampicillin and 50 μg/mL kanamycin.

The positive *E. coli* clones including *E. coli*/pET21-Strep-SCR/pET28-His-SCR2 and *E. coli*/pET21-Strep-SCR2/pET28-His-SCR3 were inoculated into 5 ml LB medium containing 100 μg/mL ampicillin and 50 μg/mL kanamycin and cultured overnight at 37° C. with shaking at 200 rpm. Then 3 mL of the culture was transferred to 150 mL LB medium supplemented with 100 μg/mL ampicillin and 50 μg/mL kanamycin at 37° C. with shaking at 200 rpm. When the $OD_{600}$ value of culture reached 0.6-0.8, IPTG was added at the various concentrations of 0.1 mM, 0.2 mM, 0.5 mM and 1.0 mM. The recombinant *E. coli* cells were then cultured for 12 hr at 30° C., and then were centrifuged at 12,000 rpm for 10 min and washed three times with physiological saline.

Example 8: Preparation of Cell Disruption Samples for Hetero-Oligomer Purification The cells of recombinant *E. coli*/pET21-Strep-SCR/pET28-His-SCR2 and *E. coli*/pET21-Strep-SCR2/pET28-His-SCR3 were collected and washed with saline, and resuspended in buffer (20 mM Tris, 150 mM NaCl, pH 8.0). The cells were then sufficiently disintegrated using a magnetic stirrer, and disrupted using an ultrasonic disrupter (Xinzhi, Ningbo, China) (disruption 2 s, stop 4 s, working time 30 min, work intensity 40%) to release the intracellular proteins. The supernatant was collected by centrifugation at 12,000×g for 40 min. The supernatant then transferred to a clean centrifuge tube prepared for protein purification after it was filtered by 0.22 μm membrane filter.

Example 9: Affinity Chromatography of Hetero-Oligomers SCR/SCR2 and SCR2/SCR3 on a Ni-NTA Column The supernatant obtained from Example 8 was first loaded on a Ni-NTA column with a binding buffer (20 mM Tris, 150 mM NaCl, pH 8.0). After additional washing with 40 mM imidazole in the binding buffer, the hetero-oligomers were eluted with 200 mM imidazole in the binding buffer.

Example 10: Purification of Hetero-Oligomers SCR/SCR2 and SCR2/SCR3 on a Streptrap HP Column The elution collected from Ni-NTA column was subjected to Streptrap HP column with a binding buffer (40 mM Tris, 150 mM NaCl, pH 8.0). After additional washing with the binding buffer, the hetero-oligomers were eluted with 2.5 mM desthiobiotin in the binding buffer.

Example 11: Reductive Activity Assay of Hetero-Oligomers Towards 2,4-Dichlorobenzophenone Enzyme activity assay system (250 ul) contained 0.5 mM NADPH, 1 mM substrate (i.e. 2,4-dichlorobenzophenone) and appropriate amount of enzyme. The reaction mixture was incubated at 30° C. for 2 min, the appropriate amount of enzyme was added, and finally the absorption change was scanned at 340 nm wavelength. The calculated relative enzyme activity of SCR/SCR2 and SCR2/SCR3 were 4.55 U/mg and 4.42 U/mg towards 2,4-dichlorobenzophenone, respectively. In contrast, no enzyme activities were detected for homo-oligomers SCR, SCR2 or SCR3.

Example 12: Reductive Activity Assay of Hetero-Oligomers Towards 2-Acetonaphthone Enzyme activity assay system (250 ul) contained 0.5 mM NADPH, 1 mM substrate (i.e. 2-acetonaphthone) and appropriate amount of enzyme. The reaction mixture was incubated at 30° C. for 2 min, the appropriate amount of enzyme was added, and finally the absorption change was scanned at 340 nm wavelength. The calculated relative enzyme activity of SCR/SCR2 was 2.43 U/mg towards 2-acetonaphthone. In contrast, no enzyme activities were detected for homo-oligomers SCR, SCR2 or SCR3.

Example 13: Reductive Activity Assay of Hetero-Oligomers Towards [(E)-2-[3-[3-[2-(7-chloro-2-quinolinyl)ethenyl]phenyl]-3-oxopropyl]benzoic acid methyl ester (Keto Easter M)

Enzyme activity assay system (250 ul) contained 0.5 mM NADPH, 1 mM substrate (i.e. [(E)-2-[3-[3-[2-(7-chloro-2-quinolinyl)ethenyl]phenyl]-3-oxopropyl]benzoic acid methyl ester (Keto Easter M) and appropriate amount of enzyme. The reaction mixture was incubated at 30° C. for 2 min, the appropriate amount of enzyme was added, and finally the absorption change was scanned at 340 nm wavelength. The calculated relative enzyme activity of SCR/SCR2 and SCR2/SCR3 were 0.86 U/mg and 1.21 U/mg towards [(E)-2-[3-[3-[2-(7-chloro-2-quinolinyl)ethenyl]phenyl]-3-oxopropyl]benzoic acid methyl ester (Keto Easter M), respectively. In contrast, no enzyme activities were detected for homo-oligomers SCR, SCR2 or SCR3.

In addition, the invention also obtained the hetero-oligomers of SCR/SCR3, which also showed some activities to polyphenyl ketones.

While the present invention has been described in some details for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A hetero-oligomer of (S)-carbonyl reductases capable of catalyzing the reduction of polyphenyl ketones, wherein said hetero-oligomer is formed by two or more isolated (S)-carbonyl reductases with different amino acid sequences which are selected from the group consisting of an isolated SCR having the amino acid sequence of SEQ ID NO: 1, an isolated SCR2 having the amino acid sequence of SEQ ID NO: 2, and an isolated SCR3 having the amino acid sequence of SEQ ID NO: 3.

2. The hetero-oligomer of claim 1, wherein said hetero-oligomer is a hetero-oligomer formed by SCR/SCR2 or SCR2/SCR3.

3. The hetero-oligomer of claim 1, wherein said hetero-oligomer of (S)-carbonyl reductases is obtained by co-expressing two or more (S)-carbonyl reductases with different amino acid sequences in the same host.

4. A method of using said hetero-oligomers of claim 1, comprising applying said hetero-oligomers to catalyze the reduction of polyphenyl ketones.

* * * * *

SEQUENCE LISTING

<160> NUMBER OF SEQ ID NOS: 11

<210> SEQ ID NO 1
<211> LENGTH: 279
<212> TYPE: PRT
<213> ORGANISM: Candida parapsilosis

<400> SEQUENCE: 1

```
Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val His Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
                100                 105                 110

Asp Val Phe Val Ala Asn Ala Gly Val Thr Trp Thr Gln Gly Pro Glu
            115                 120                 125

Ile Asp Val Asp Asn Tyr Asp Ser Trp Asn Lys Ile Ile Ser Val Asp
        130                 135                 140

Leu Asn Gly Val Tyr Tyr Cys Ser His Asn Ile Gly Lys Ile Phe Lys
145                 150                 155                 160

Lys Asn Gly Lys Gly Ser Leu Ile Ile Thr Ser Ser Ile Ser Gly Lys
                165                 170                 175

Ile Val Asn Ile Pro Gln Leu Gln Ala Pro Tyr Asn Thr Ala Lys Ala
            180                 185                 190

Ala Cys Thr His Leu Ala Lys Ser Leu Ala Ile Glu Trp Ala Pro Phe
        195                 200                 205

Ala Arg Val Asn Thr Ile Ser Pro Gly Tyr Ile Asp Thr Asp Ile Thr
    210                 215                 220

Asp Phe Ala Ser Lys Asp Met Lys Ala Lys Trp Trp Gln Leu Thr Pro
225                 230                 235                 240

Leu Gly Arg Glu Gly Leu Thr Gln Glu Leu Val Gly Gly Tyr Leu Tyr
                245                 250                 255

Leu Ala Ser Asn Ala Ser Thr Phe Thr Thr Gly Ser Asp Val Val Ile
            260                 265                 270

Asp Gly Gly Tyr Thr Cys Pro
        275

<210> SEQ ID NO 2
<211> LENGTH: 279
<212> TYPE: PRT
<213> ORGANISM: Candida parapsilosis

<400> SEQUENCE: 2

Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95
```

```
Ser Val Glu Glu Thr Ile Ser Gln Gln Glu Lys Asp Phe Gly Thr Ile
            100                 105                 110

Asp Val Phe Val Ala Asn Ala Gly Val Pro Trp Thr Glu Gly Pro Glu
            115                 120                 125

Ile Asn Val Asp Asn Tyr Asp Ser Trp Asn Lys Ile Ile Asn Leu Asp
130                 135                 140

Leu Asn Gly Val Tyr Tyr Cys Ala His Thr Val Gly Lys Ile Phe Lys
145                 150                 155                 160

Lys Asn Gly Lys Gly Ser Leu Val Ile Thr Ser Ser Met Ser Gly Thr
                165                 170                 175

Ile Val Asn Val Pro Gln Leu Gln Ala Ala Tyr Asn Ala Ala Lys Ala
            180                 185                 190

Ala Cys Thr His Leu Thr Lys Ser Leu Ala Val Glu Trp Ala Pro Phe
            195                 200                 205

Ala Arg Val Asn Cys Val Ser Pro Gly Tyr Ile Ala Thr Glu Ile Ser
            210                 215                 220

Asp Phe Val Glu Lys Asp Met Lys Ala Lys Trp Trp Gln Leu Thr Pro
225                 230                 235                 240

Leu Gly Arg Glu Gly Leu Ala Gln Glu Leu Val Gly Ala Tyr Leu Tyr
                245                 250                 255

Leu Ala Ser Asn Ala Ser Thr Tyr Thr Thr Gly Ala Asn Leu Ala Val
                260                 265                 270

Asp Gly Gly Tyr Thr Cys Pro
                275

<210> SEQ ID NO 3
<211> LENGTH: 279
<212> TYPE: PRT
<213> ORGANISM: Candida parapsilosis

<400> SEQUENCE: 3

Met Gly Glu Ile Glu Ser Tyr Cys Asn Lys Leu Gly Pro Leu Pro
1               5                   10                  15

Thr Lys Ala Pro Thr Leu Ala Lys Asn Val Leu Asp Leu Phe Ser Leu
            20                  25                  30

Lys Gly Lys Val Ala Ser Val Thr Gly Ser Ser Gly Gly Ile Gly Trp
            35                  40                  45

Ala Val Ala Glu Ala Tyr Ala Gln Ala Gly Ala Asp Val Ala Ile Trp
            50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Ile Pro Trp Ala Asp Gly Pro Val
            115                 120                 125

Ile Asp Leu Glu Asn Tyr Asp Ala Trp Asn Lys Leu Ile Asn Thr Asp
130                 135                 140

Ile Asn Gly Val Phe Tyr Cys Ala His Ser Ile Gly Lys Ile Phe Lys
145                 150                 155                 160

Lys Asn Gly Lys Gly Ser Leu Ile Ile Thr Ala Ser Leu Ala Gly Ser
                165                 170                 175

Val Val Thr Ile Pro Gln Gln Gln Thr Pro Tyr Asn Thr Ala Lys Ala
```

```
            180                 185                 190
Ala Cys Leu His Leu Ala Lys Ser Leu Ala Val Glu Trp Ala Pro Phe
        195                 200                 205

Ala Arg Val Asn Thr Val Ser Pro Gly Tyr Phe Glu Thr Glu Ile Asn
        210                 215                 220

Gly Phe Ala Asp Glu Asp Met Arg Glu Lys Trp Tyr Gln Leu Thr Pro
225                 230                 235                 240

Leu Gly Arg Met Gly Ile Thr Glu Glu Leu Val Gly Gly Tyr Leu Tyr
                245                 250                 255

Phe Ala Ser Asn Ala Ser Thr Phe Thr Thr Gly Ser Asp Leu Ile Ile
            260                 265                 270

Asp Gly Gly Phe Thr Cys Pro
        275

<210> SEQ ID NO 4
<211> LENGTH: 60
<212> TYPE: DNA
<213> ORGANISM: artificial sequence
<220> FEATURE:
<223> OTHER INFORMATION: DNA primer

<400> SEQUENCE: 4
atcggatccg tggtctcatc ctcaatttga aaagggttct atgggcgaaa tcgaatctta     60

<210> SEQ ID NO 5
<211> LENGTH: 32
<212> TYPE: DNA
<213> ORGANISM: Artificial Sequence
<220> FEATURE:
<223> OTHER INFORMATION: DNA primer

<400> SEQUENCE: 5
tgactctcga gctatggaca cgtgtatcca cc                                   32

<210> SEQ ID NO 6
<211> LENGTH: 60
<212> TYPE: DNA
<213> ORGANISM: Artificial Sequence
<220> FEATURE:
<223> OTHER INFORMATION: DNA Primer

<400> SEQUENCE: 6
atcggatccg tggtctcatc ctcaatttga aaagggttct atgggcgaaa tcgaatctta     60

<210> SEQ ID NO 7
<211> LENGTH: 34
<212> TYPE: DNA
<213> ORGANISM: Artificial Sequence
<220> FEATURE:
<223> OTHER INFORMATION: DNA Primer

<400> SEQUENCE: 7
tgactctcga gctatggaca agtgtaacca ccat                                 34

<210> SEQ ID NO 8
<211> LENGTH: 50
<212> TYPE: DNA
<213> ORGANISM: Artificial Sequence
<220> FEATURE:
<223> OTHER INFORMATION: DNA Primer

<400> SEQUENCE: 8
cgcggatccg aaaatttata tttccagagt atgggcgaaa tcgaatctta                50
```

```
<210> SEQ ID NO 9
<211> LENGTH: 32
<212> TYPE: DNA
<213> ORGANISM: Artificial Sequence
<220> FEATURE:
<223> OTHER INFORMATION: DNA Primer

<400> SEQUENCE: 9
tgactctcga gctatggaca cgtgtatcca cc                          32

<210> SEQ ID NO 10
<211> LENGTH: 50
<212> TYPE: DNA
<213> ORGANISM: Artificial Sequence
<220> FEATURE:
<223> OTHER INFORMATION: DNA Primer

<400> SEQUENCE: 10
ccggaattcg aaaatttata tttccagagt atgggcgaaa tcgaatctta       50

<210> SEQ ID NO 11
<211> LENGTH: 35
<212> TYPE: DNA
<213> ORGANISM: Artificial Sequence
<220> FEATURE:
<223> OTHER INFORMATION: DNA Primer

<400> SEQUENCE: 11
gcccgctcga gctatggaca ggtgaatcca ccatc                       35
```